(12) United States Patent
Fang (10) Patent No.: US 7,027,398 B2
(45) Date of Patent: Apr. 11, 2006

(54) METHOD AND APPARATUS FOR MONITORING VOICE CONVERSATIONS FROM CUSTOMER PREMISES EQUIPMENT

(75) Inventor: Zheng Fang, Horsham, PA (US)

(73) Assignee: General Instrument Corporation, Horsham, PA (US)

( * ) Notice: Subject to any disclaimer, the term of this patent is extended or adjusted under 35 U.S.C. 154(b) by 848 days.

(21) Appl. No.: 09/833,291

(22) Filed: Apr. 12, 2001

(65) Prior Publication Data

US 2002/0150081 A1   Oct. 17, 2002

(51) Int. Cl.
*H04L 12/26* (2006.01)

(52) U.S. Cl. .................. 370/235; 370/356; 379/35; 709/226

(58) Field of Classification Search ........... 370/409, 370/260, 241, 33, 390, 389, 356, 352, 235; 709/226; 379/35
See application file for complete search history.

(56) References Cited

U.S. PATENT DOCUMENTS 5,590,171 A * 12/1996 Howe et al. ............... 379/33
5,627,819 A * 5/1997 Dev et al. .................. 370/250
6,560,224 B1 * 5/2003 Kung et al. ................ 370/356
6,563,797 B1 * 5/2003 Kung et al. ................ 370/252
6,621,800 B1 * 9/2003 Klein ........................ 370/282
6,647,096 B1 * 11/2003 Milliorn et al. ............. 379/35

* cited by examiner

*Primary Examiner*—Brian Nguyen
*Assistant Examiner*—Tri H. Phan
(74) *Attorney, Agent, or Firm*—Lawrence T. Cullen (57) ABSTRACT

An apparatus and associated method for monitoring telephone communications from the customer premises equipment (CPE) (and the subscriber telephone equipment attached thereto) in a VoIP system. The apparatus comprises a real time protocol mirror. The real time protocol (RTP) mirror is included in the CPE and can be controllably altered between two mirror states. The RTP mirror provides for original RTP packet transmission between a plurality of CPEs in both the first mirror state and the second mirror state. In the first mirror state the RTP mirror limits the transmission of a copy RTP packet from the RTP mirror. In the second mirror state the RTP mirror provides for transmission of the copy RTP packet. The apparatus may also include a network and a RTP server. The network transfers copy RTP packets to or from the CPE to the RTP server. The RTP server is located on the network to receive the copy RTP packets generated by the RTP mirror.

18 Claims, 6 Drawing Sheets

METHOD AND APPARATUS FOR MONITORING VOICE CONVERSATIONS FROM CUSTOMER PREMISES EQUIPMENT

FIELD OF THE INVENTION

This invention relates to telephony system, and more particularly to monitoring voice communications passing over telephony systems.

BACKGROUND OF THE INVENTION

Plain Old Telephone Systems (POTS) represent the traditional analog phone service. Certain types of digital phone systems have been developed. One such digital telephone system is Voice over Internet (VoIP) system that use digital signal transmission techniques to transmit voice communications at least partially over the Internet. VoIP provide such promising benefits as reduced cost and improved functionality for long distance communications that result partially from: reduced Internet voice transmission costs compared to the cost of POTS voice transmission by long distance exchange carriers, increased signal processing and call set-up and operating capability, and enhanced signal encryption and signal processing techniques that result from the digital nature of the VoIP communications. The use of VoIP provides challenges for lawful voice monitoring of subscription telephones communicating over VoIP systems by such groups as the police and the Federal Bureau of Investigation since the VoIP data routes do not always follow a single path.

It would therefore be desirable to configure the VoIP equipment to provide for monitoring of customer premises equipment (CPE) by legal lawful groups.

SUMMARY OF THE INVENTION

The present invention is directed to an apparatus and associated method for monitoring telephone communications from customer premises equipment (CPE) in a VoIP system. The apparatus includes a real time protocol (RTP) mirror integrated in the CPE that can be controllably altered between two mirror states. The RTP mirror permits for transmission of the original RTP packet to or from the CPE in both mirror states. In the first mirror state the RTP mirror limits the transmission of a copy RTP packet from the RTP mirror. In the second mirror state the RTP mirror provides for transmission of that copy RTP packet. The apparatus may also include a network and a RTP server. The network transfers the copy RTP packets to or from the CPE. The RTP server is located on the network to receive the copy RTP packets generated by the RTP mirror.

BRIEF DESCRIPTION OF THE DRAWINGS

The accompanying drawings, which are incorporated herein and constitute part of this specification, illustrate the presently preferred embodiment of the invention and, together with the general description given above and the detailed description given below, serve to explain features of the invention.

DETAILED DESCRIPTION OF THE EMBODIMENT

This disclosure describes monitoring of telephone systems by lawful groups, or agencies such as the police. The structure and operation of the Voice over Internet (VoIP) system 100, that represents one embodiment of digital telephone system, is described. The techniques by which the VoIP system is monitored is also described. The expression "customer premises equipment" (CPE) and "consumer premises equipment" (CPE) are used interchangeably throughout this description along with the Figures herein described.

Figure 1:
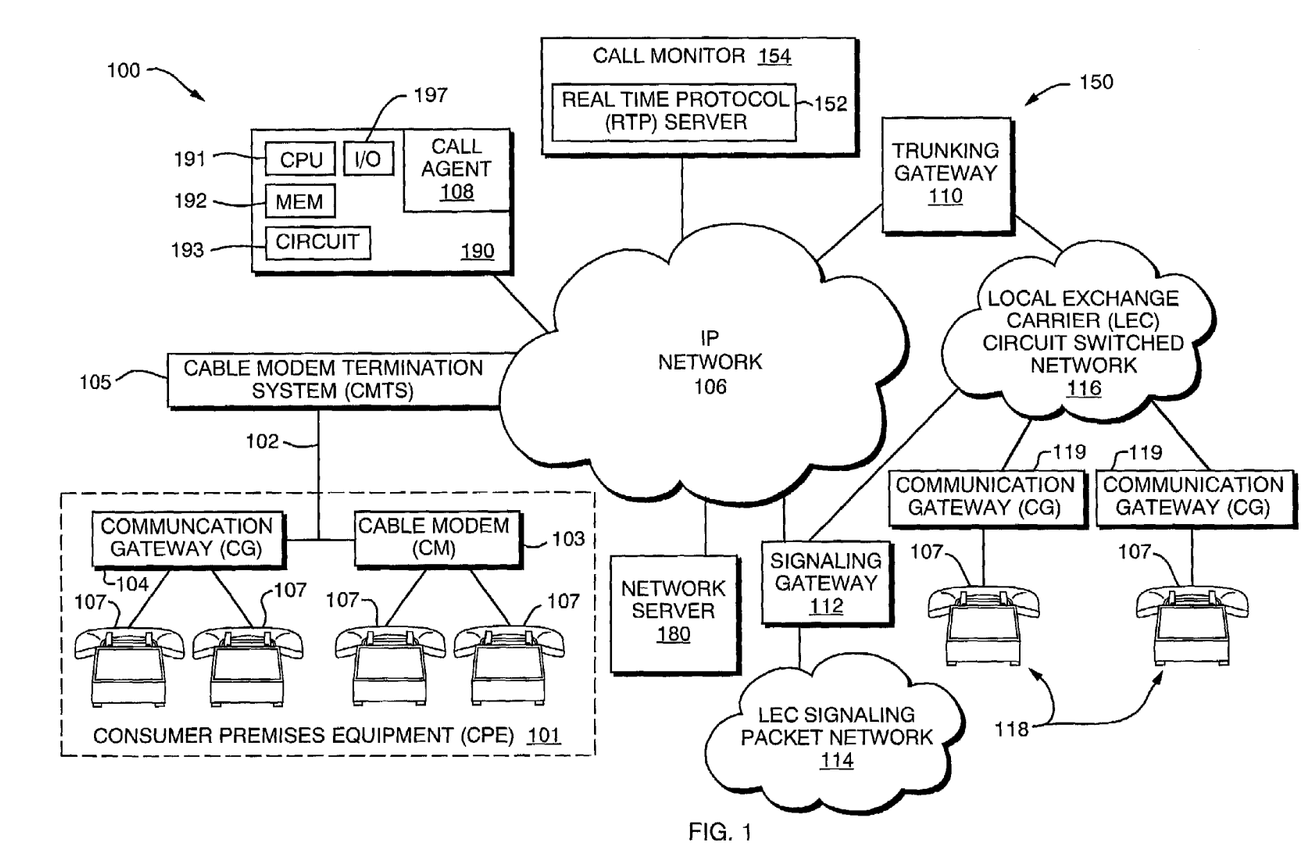
FIG. 1 is a block diagram of one embodiment of a Voice over Internet (VoIP) system.

FIG. 1 shows one embodiment of voice over Internet (VoIP) system 100. The VoIP system 100 provides for voice communication between a plurality of consumer premises equipment (CPE) 101 over an Internet (IP) network 106 and a hyper fiber coax network (HFC) 102. Alternatively, the VoIP system 100 provides for voice communication between a CPE 101 and a CPE 118 over the IP network 106, the HFC 102, and a LEC circuit switched network 116. The CPE 101 is configured to include, e.g., a cable modem 103 and a subscriber telephone 107, or any other communication device such as a communications gateway 104 that allows for subscriber telephone 107 to communicate over the IP network 106. A HFC 102 is configured to provide optic-based cable communications between the local CPE 101 and a cable modem termination system (CMTS) 105.

The embodiment of VoIP system 100 shown in FIG. 1 includes the CPE 101 (that includes the cable modem 103, the HFC 102, the CMTS 105, the IP network 106, one or more subscriber telephones 107, a call agent 108, a trunking gateway 110, a signaling gateway 112, a local exchange carrier (LEC) signaling packet network 114, a LEC circuit switched network 116, a remote CPE 118, and a plurality of subscriber telephones 107 coupled to the CPE 118. The CPE 118 includes, e.g., a cable modem 119. The VoIP system 100 provides communication using the IP network 106 between subscriber telephones 107 connected to the CPE 101 and/or the remote CPE 118.

Figure 2:
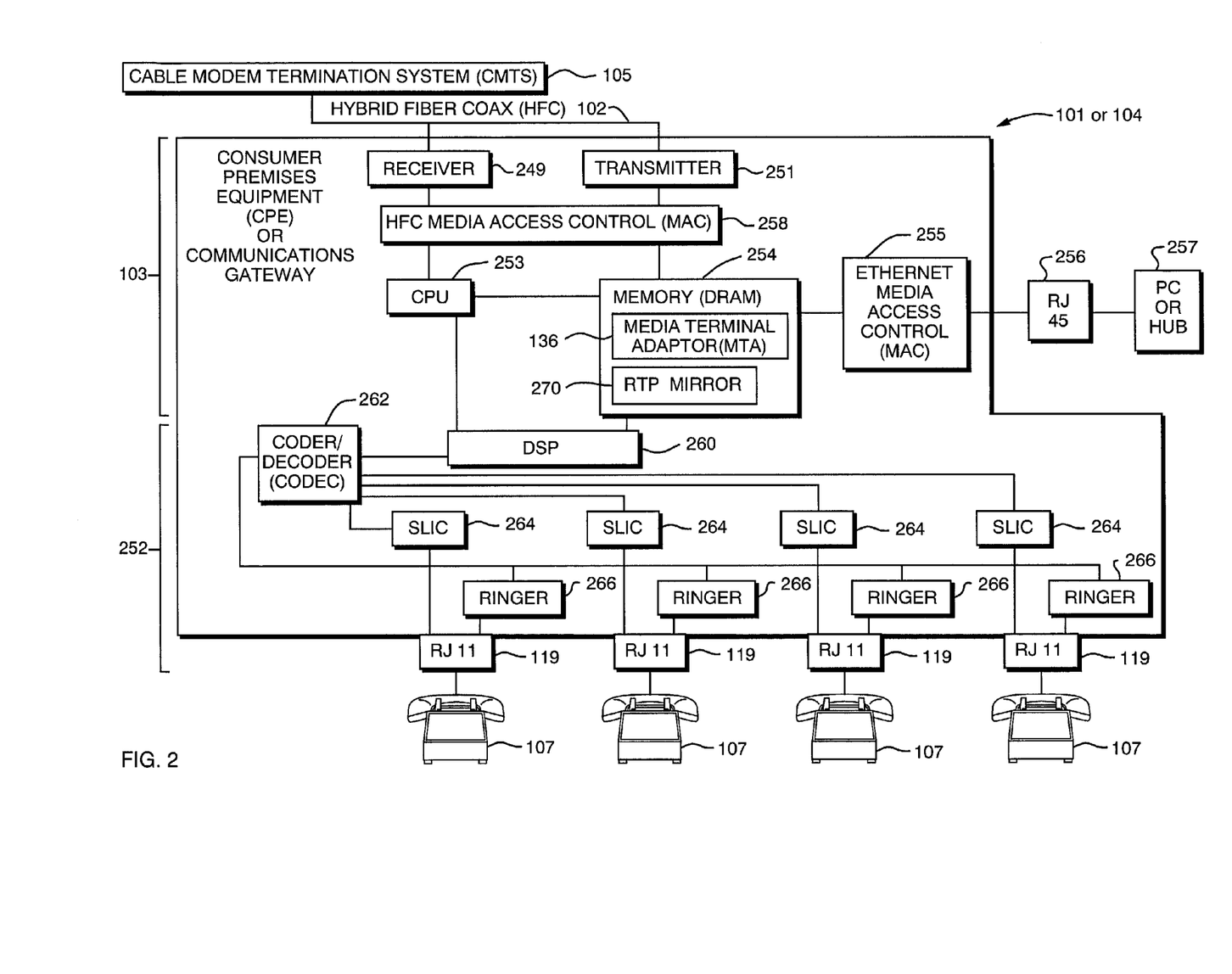
FIG. 2 shows one embodiment of consumer premises equipment (CPE) shown in the FIG. 1 VoIP system.

The HFC 102 allows for the cable modem 103 to communicate via the CMTS 105 over the IP network 106. This disclosure describes the interaction between one embodiment of CPE 101, as shown in FIG. 2, and other portions of the VoIP system 100. The HFC 102 allows for data and IP voice to share the bandwidth with television channels. The CPE 101 includes one or a plurality of telephone end points to which the subscriber telephone 107 connects. The CMTS 105 can be configured to provide for data, cable TV and/or telephone applications.

One embodiment of HFC 102 uses the Data Over Cable Systems Interface Specification (DOCSIS) protocol. DOCSIS is a standard for the cable modem interface over the HFC 102 between a cable TV operator and a computer or subscriber telephone. DOCSIS has been accepted as a standard since DOCSIS 1.0 when it was ratified by the International Telecommunication Union (ITU) in March of 1998. Cable modems conforming to DOCSIS are commercially available from a variety of vendors.

Different embodiments of telephone service use the VoIP system 100. One embodiment of VoIP service is referred to as "on-net calls," in which multiple CPEs 101 communicate using the IP network 106 and/or the HFC 102 only. Another embodiment of VoIP telephone service is referred to as "off-net calls" in which a CPE 101 communicates with the remote CPE 118 over a hybrid network system including the LEC circuit switched network 116 portion and the IP network 106. Off-net calls involve not only the IP network 106 and the HFC 102 as do on-net calls, but also involve a LEC circuit switched network 116, a trunking gateway 110, and the signaling gateway 112 as shown in FIG. 1.

The call agent 108 initiates and terminates the calls in the IP network 106. There is typically a plurality of call agents 108 connected to the IP network 106; a different service provider may operate each call agent. Each call agent may use a different call control language, such as Network Control System (NCS), Simple Gateway Control Protocol (SGCP), Multimedia Gateway Control Protocol (MGCP), GR303, and others. The call agent acts as a master of set-up and teardown for VoIP voice communications. A plurality of call agents 108 is provided across the IP network.

The embodiment of call agent 108 shown in FIG. 1 is physically structured as a computer including the hardware to provide the necessary signals to initiate, monitor, regulate, and terminate VoIP communication. The call agent 108 interacts with a media terminal adapter 136 that is included in the CPE 118, as shown in the embodiment of FIG. 2. Each call agent 108 maintains the call state, performs phone number to IP address translations, and implements class features. One embodiment of the call agent 108 is fashioned as a server that runs an operating system such as a UNIX or WINDOWS NT® (A registered trademark of Microsoft Corporation of Redmond, Wash.). The call agent 108 may be configured as a server, a stand-alone computer, a PC, or any type of computer having adequate processing, memory and I/O capabilities. The call agent 108 includes a programmable central processing unit (CPU) 191 that is operable with a memory 192 (e.g., RAM, ROM, hard disk and/or removable storage) and well-known support circuits 193 such as power supplies, clocks, cache, and the like. Additionally, the call agent 108 includes I/O circuits 197 that produce control signals, such as a control output signal, and receive signals such as an input signal. By executing software stored in the memory 192, the call agent 108 interfaces with the CPEs 101, the subscriber telephones 107, and the real time protocol (RTP) server 152 that leads to call set-up, call termination, voice transmission, and other features that provide for telephone communication over the VoIP system.

The media terminal adapter (MTA) 136 acts under the control of the call agent 108. The MTA is integrated in the cable modem 103. The MTA 136 is controlled by the respective call agent 108 to monitor for events occurring at the subscriber telephone 107, and report events (e.g., an off-hook condition). The MTA 136 sets up and tears down RTP streams as commanded. Each call agent 108 operates independently under the control of an associated service provider to command its respective MTA 136 to monitor VoIP events, establish signal tones, and set up or tear down real time protocol (RTP) voice streams.

If, however, an off-net call is being made, then the VoIP system 100 has to establish communications to a Local Exchange Carrier (LEC) network portion 150 as well as the IP network 106. Central offices included in the LEC circuit switched network 116 are used to set-up and break down the calls in the LEC circuit switched network 116 portion of the VoIP system. The communications between the IP network 106 and the LEC circuit switched network 116 can be categorized to include signal and voice communication portions. The signal communications establish and break down channels by which the voice communications are transmitted. In one embodiment of off-net calls, the signal and the voice packets follow different routes (e.g. over the retrunking gateway 110 and the signaling gateway 112) between the IP network and the LEC circuit switched network 116.

The trunking gateway 110 shown in FIG. 1, provides for voice communication interconnection those portions of the VoIP system 100 that use the IP network (and communicate using the real time protocol (RTP) protocol) and those portions of the VoIP system that use the LEC circuit switched network 116 (and communicate using the phase code modulation (PCM) protocol). The trunking gateway 110 converts voice packets between the RTP packets used in the IP network 106 and the phase code modulation (PCM) packets used in the LEC circuit switched network 116. The trunking gateway 110 sets up, maintains, and tears down voice steams provided between the IP network and the LEC circuit switched network 116.

The trunking gateway 110 thus has to provide for a mapping between the portions of the network that use the real time protocol (RTP) from those portions of the network that use the PCM protocol. The trunking gateway 110 sets up and tears down RTP and PCM steams, as commanded by the call agent 108. The trunking gateway 110 therefore acts as a slave to either the call agent 108 in the IP network 106 or the central office (not shown) in the LEC circuit switched network. The trunking gateway 110 also monitors the RTP packets in RTP streams transmitted between the IP network 106 and the LEC circuit switched network 116.

The LEC signaling packet network 114 controls the signaling provided over the signaling gateway 112 between the IP network 106 and the LEC circuit switched network 116. The signals will be transmitted between the IP network and the LEC circuit switched network 116 will result in the set up and break down of off-net calls via the signaling gateway.

FIG. 2 shows one embodiment of CPE 101 as shown in FIG. 1. The CPE includes the cable modem portion 103, a telephony interface portion 252, a central processing unit (CPU) 253, a memory 254, a receiver 249, and a transmitter 251. The cable modem portion 103 is configured to provide IP network data communications to, e.g., via an Ethernet media access control (MAC) 255 and a high speed data port RJ45 (Ethernet) computer connector 256 to a computer or hub 257 or via one or more RJ11 connectors to one or more subscriber telephone 107.

The cable modem portion 103 also includes a hybrid or hyper fiber coax media access control (HFC MAC) 258 that provides OSI layer 2 interface between the HFC 102 and the combined memory 254 and CPU 253. An Ethernet MAC 255 provides an interface between a PC or hub 257 and the CPU 253/memory 254. The telephony interface portion 252 is configured to provide IP network voice communications to, e.g., one or more subscriber telephones 107. The CPU 253 controls and manages the processes occurring within the CPE 101 by data transfer and data storage between the components of the CPE.

In one embodiment, the cable modem portion 103 includes a chip that integrates many of the above components. For example, Broadcomm Corporation of Irvine, Calif. produces one commercially available cable modem chip as the BCM3350 that combines the integrated 64/256-Quadrature Amplitude Modulation (QAM) receiver 249, a Quadrature Phase Shift Keying (QPSK)/16-Quadrature Amplitude Modulation (QAM) transmitter 251, a complete DOCSIS HFC media access control (MAC) 258, a MIPS32 CPU 253, and a memory 254.

The receiver 249 directly samples a tuner output using an integrated pin grid array (PGA) package and analog to digital (A/D) converter, digitally resamples and demodulates the signal using recovered clock and carrier timing, filters, and equalizes the data. The soft decisions resulting from the sampling are passed to a compatible decoder. The final received data stream from the receiver 249 is delivered in MPEG-w transfer format. All gain, clock, and carrier acquisition and tracking loops are integrated in the receiver. The transmitter 251 takes burst or continuous data, provides encoding and pre-equalization for the DOCSIS application, filters, and modulates the data stream, and provides a direct analog output to the HFC.

The telephony interface portion 252 includes a digital signal processor (DSP) 260, a coder/decoder (CODEC) 262, a plurality of subscriber line interface channels (SLIC) 264, a plurality of ringers 266, and a plurality RJ11 telephone jacks 119. One subscriber telephone 107 may fit within each one of the plurality of RJ11 telephone jacks 119. The ringer 266 produces a ring in a prescribed subscriber telephone 107 when called from another subscriber telephone 107.

The DSP 260 performs such voice protocol processing as compression, decompression, dial tone generation, Dual Tone Multi-Frequency (DTMF) tone detection, echo cancellation, etc. The DSP generates phase code modulation (PCM) signals what are sent to the CODEC 262. The DSP 260 also processes received PCM signals originating from the subscriber telephone 107 via the CODEC 262, and transfers the processed signal to the cable modem portion 103. The DSP is commercially available from such companies as Motorola, Inc. of Schaumburg, Ill. and Texas Instruments of Dallas, Tex.

The digital interface between the DSP 260 and the CODEC 262 uses pulse code modulation (PCM). The CODEC 262 receives digital information from the DSP 260 in the form of a bit-stream where, in one embodiment, the amplitude of the incoming signal is related to the digital value (e.g., a digital 0 or 1) being sent. The CODEC 262 processes the PCM signals from the DSP 260, and generates an analog signal that is transmitted to the appropriate SLICs. In signals originating at the subscriber telephone, the CODEC 262 samples the signal from the SLIC 264 and translates the discrete amplitude into a digital number that is sent to the DSP, thereby translating the audio signals received from the SLIC into phase code modulated (PCM) signals that can be transferred to the DSP. The CODEC 262 transmits data to, and receives data from, the DSP utilizing the CODEC pins. The frame sync signals determine the frame's start position and the channel data that will be transmitted.

One SLIC 264 acts to connect the CPE 101 with one subscriber telephone 107. The appropriate SLIC 264 translates the analog signals received from the CODEC 262 into voice signals (voltage levels) that can be converted by the subscriber telephone into voices or audible noises. The SLIC 264 also transfers audio signals from the microphone of the subscriber telephone 107 to analog signals that are received, and processed by, the CODEC. The SLIC 264 provides an interface between the RJ11 telephone jack 268 and the CODEC 262. The SLIC 264 interfaces with the CPU 253 by sending an interrupt to the CPU, when necessary. The SLIC uses the interrupt to inform the CPU of the occurrence of events at the subscriber telephone. The SLIC 264 also contains circuits for loop-back testing that is used to test the operation of the subscriber telephone 107. The SLIC 264 also performs signal echo reduction as signals encounter conductor discontinuities by flowing through portions of the CPE 101.

The memory 254 may include RAM or ROM portions. More particularly, the memory 254 includes a dynamic RAM (DRAM) that is configured to perform a variety of operations. Certain ones of the operations stored in the memory 254 that may be accessed using the CPU 253 include the real time protocol (RTP) mirror 270 and the media terminal adapter (MTA) 136. The RTP mirror can be viewed as controllably generating copy RTP packets that are copies of original RTP packets that are transmitted between multiple subscriber telephones. The RTP mirror 270 can be enabled under the remote influence of a RTP server 152. Enabling or disabling the RTP mirror does not effect the transmission of the original RTP packets. The RTP mirror, in all of its mirror states, allows the original real time protocol (RTP) packets to travel between the communicating CPEs 101 whether or not the RTP mirror is enabled.

Actuating the RTP mirror 270, by comparison, determines whether or not copy RTP packets are transferred to the RTP server 152. If the RTP mirror 270 is actuated, the copy RTP packets will be transmitted from the RTP mirror of the CPE 101a to the RTP server 152. The RTP server 152 can either play, record, store, or transfer the copy RTP packets received from the RTP mirror 270, as desired. For example, in one embodiment, the RTP server 152 can be configured as a standalone PC resident on the IP network or the HFC 102. The standalong PC could use an audio card to play the conversations occurring between the two CPE 101a and 101b to perform a legal "wiretapping" operation. As described, call agent 108, each CPE 101, and each RTP server 152 is configured in one embodiment as a computer with sufficient processing power and memory storage capability to handle the data transfer and storage associated with the operation of the VoIP system 100. The copy RTP packets received by the RTP server 152 could be played, stored, and/or then transferred over the Internet to another location.

For instance, the RTP mirror 270 is configured, whether actuated or deactuated, to provide for the passage of original RTP packets between the CPE 101 and the CPE 118. In addition, the RTP mirror when actuated selectively generates an identical copy RTP packet of the original RTP. Deactuating the RTP mirror 270 acts to limit any transmission of copy RTP packets from the CPE 101a. More particularly, the RTP server 152 does not receive any copy packets from the RTP mirror 270 if the RTP mirror is deactuated.

Figure 3:
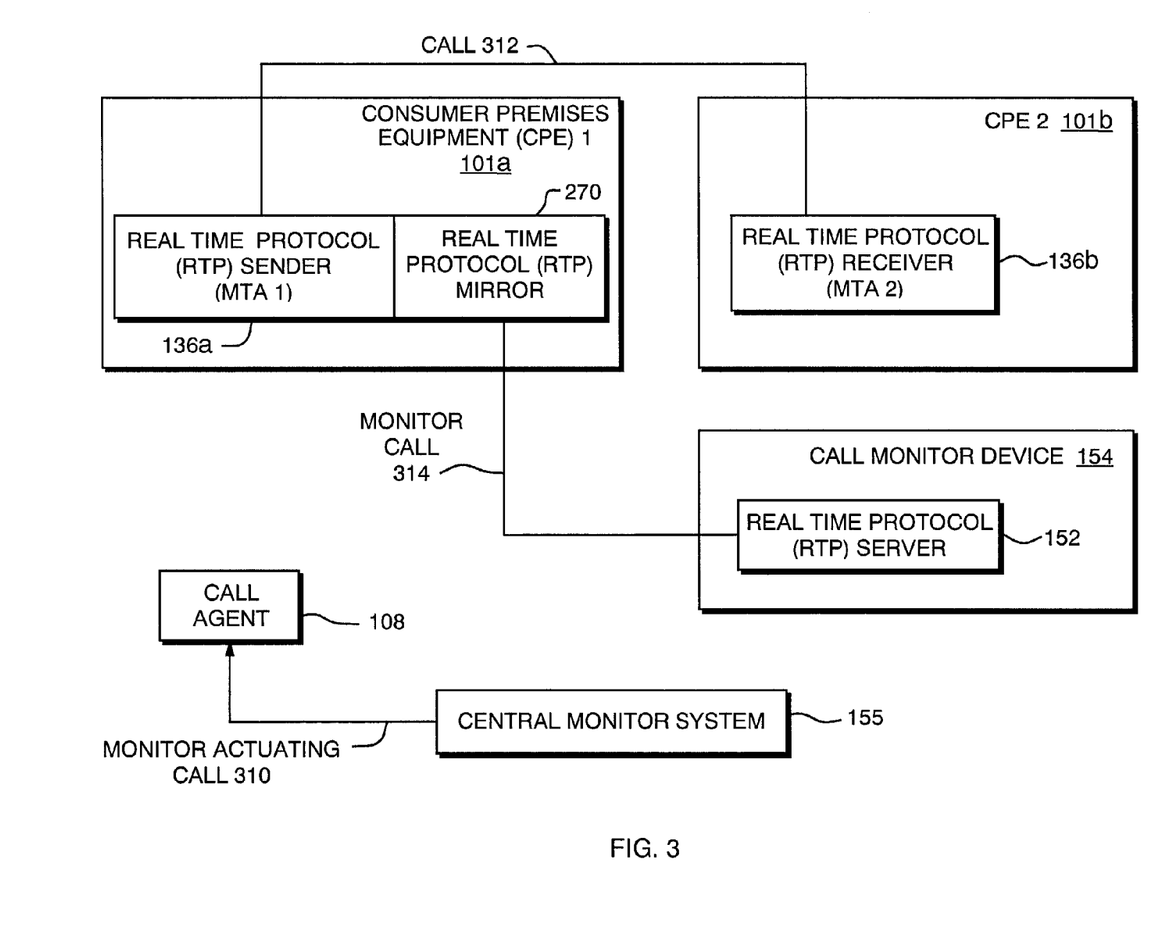
FIG. 3 shows a simplified signal block diagram showing one embodiment of "calls" established in the VoIP system of FIG. 1 between a plurality of consumer premises equipment (CPE) and "monitoring" that plurality of calls using a real time protocol (RTP) server.

FIG. 3 shows one embodiment of a plurality of CPE, 101 as 101a and 101b, in association with several other components that were shown in FIG. 1. A signal order diagram is provided between the plurality of CPEs 101a, 101b in an embodiment of the VoIP system 100. Each CPE 101a, 101b is in direct communication with either the IP network 106, the HFC 102, or the LEC circuit switched network 116 shown in FIG. 1. By communicating over only either the IP network 106 or the HFC 102, the telephone communication between the CPE 101a and the CPE 101b is characterized as an on-net call.

Figure 4:
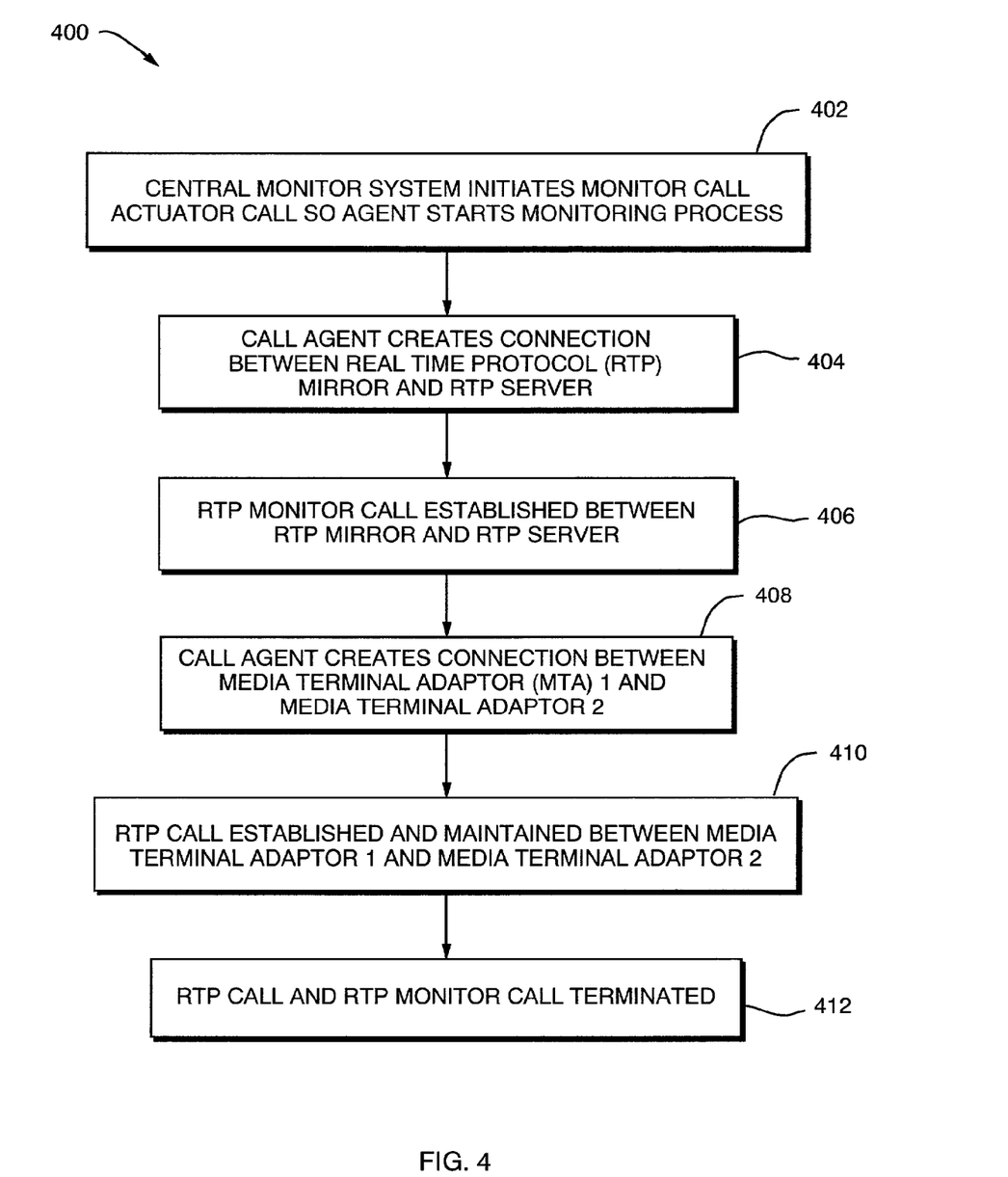
FIG. 4 shows one embodiment of a flow chart describing the procedure followed by the VoIP system of FIG. 1 in performing the signal block diagram shown in FIG. 3.

FIG. 3 also shows one embodiment of the call, monitor call, and monitor actuating call system that is established between the different components of the VoIP system 100 of FIG. 1. FIG. 3 should be read in conjunction with FIG. 4 and FIG. 5 which shows, respectively, the logic performed by the VoIP system 100 and a signal diagram between the different components of the VoIP system 100. In FIG. 4, starts with step 402 in which the central monitor system 155 initiates a monitor actuating call 310 (shown in FIG. 3) to the call agent 108 so that the call agent 108 can start configuring the VoIP system in a manner so that the communications between CPE 101a and CPE 101b are monitored. The monitor actuating call 310 forwarded to the call agent 108 will include options that indicate the identity of the CPE 101a to monitor. Any original RTP packet transmitted to or from the CPE 101a, during those periods when the CPE 101a is being monitored, will be have a copy RTP packet transmitted by the RTP mirror, and transmitted to the remote RTP server 152.

Monitoring phone communications between two CPEs involves the use of two calls as shown in FIG. 3. The first step 310 is a monitoring request is transmitted from the central monitor system 155 to the call agent 108, and which indicates the identity of the CPE 101a to be monitored. The first call is the actual call 312 established between the two communicating CPEs 101a and 101b. The call 312 is established between the media terminal adapters (MTA) 136a and 136b of each respective CPE 101a and 101b. The media terminal adapter 136a may be considered as a RTP sender, while the media terminal adapter 136b is shown in CPE 101b may be considered as the RTP receiver. Since both MTAs 136a and 136b are capable of initiating, and maintaining, full duplex communications, both the RTP sender and the RTP receiver function are performed concurrently by both MTAs 136a and 136b. The RTP sender and receiver should therefore both be viewed as a transceiver, and not a designated sender or receiver. The term RTP sender is associated with the MTA 136a, and only indicates that particular MTA which established the initial communication between the CPE 101a and the CPE 101b. Similarly, the MTA 136b that is referred to as the RTP receiver is the MTA that received the initial communication.

The second call shown in FIG. 3 that is used to monitor the phone conversations is a monitor call 314, and occurs between the RTP mirror 270 and the RTP server 152. The monitor call 314 translates copies of all the original packets that have been transmitted in 312 between the MTA 136a and the MTA 136b, in either direction. In one embodiment, the call monitor device 154 is configured as a personal computer with an audio card. Such a call monitor device could play back the audio contained within the RTP packets that were transmitted over monitor call 314. As such, both sides of the full duplex communication of the call 312 between MTA 136a and the MTA 136b are reflected, using the RTP mirror 270, to form the identical monitor call 314 that is received by the RTP server 152.

Figure 5:
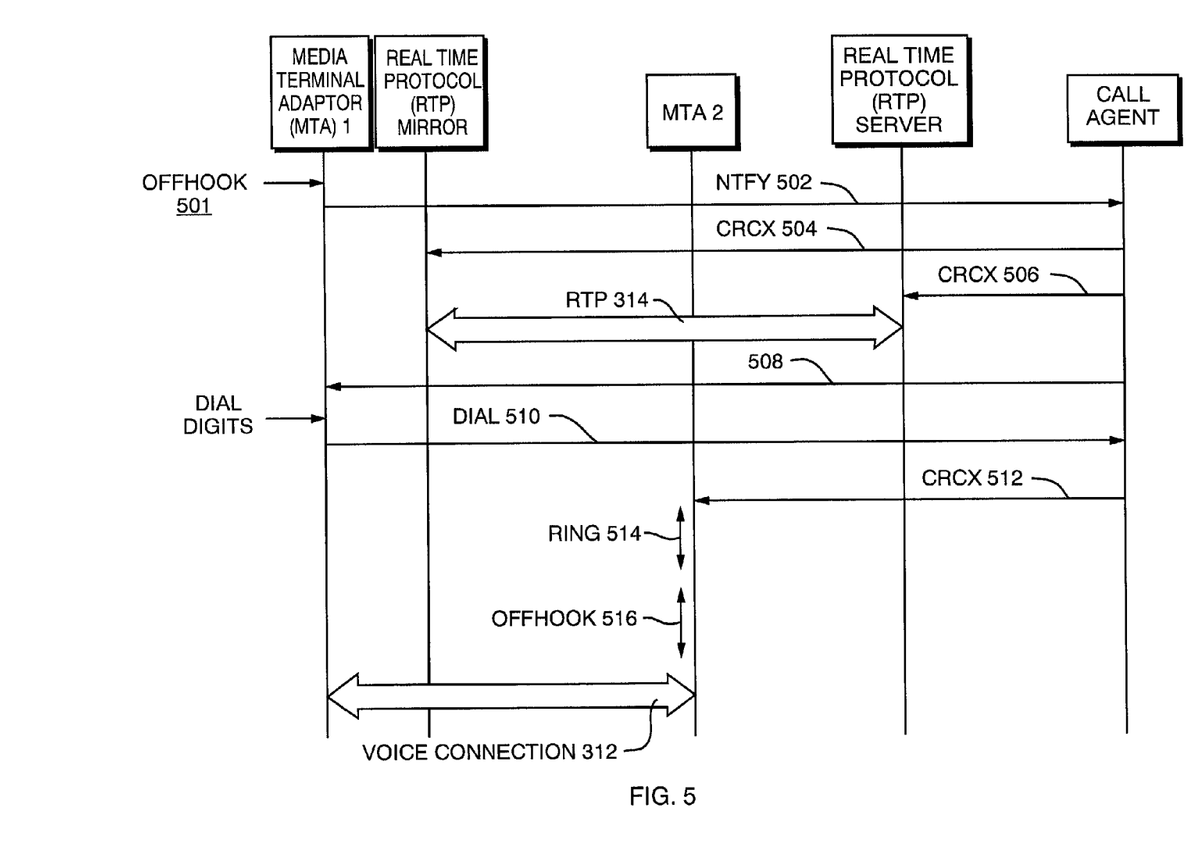
FIG. 5 shows one embodiment of a signal diagram displaying the transmitted signal communications between different components of the VoIP system of FIG. 1.

As shown in the embodiment of FIG. 4, the central monitor system initiates the monitor actuating call 310 so that the call agent 108 can commence that monitoring process shown in step 402. The method 400 shown in FIG. 4 continues to step 404 in which the call agent creates a connection between the RTP mirror and the RTP server. The notify "NTFY" signal 502 is transmitted from the MTA 136a to the MTA 136b as shown in FIG. 5. The NTFY signal 502 is sent after the CPE 101a shown in FIG. 3 goes off hook as shown by 501. The call agent 108, in response to the NTFY signal 502, sends a create connection to call mirror signal "CRCX" 504. In addition, call connection to RTP server signal 508 is also provided between the call agent 108 and the RTP server 152. The combination of the signals 502, 504, and 506 interact to establish the RTP monitor call 314 established between the RTP mirror 270 and the RTP server 152, as shown in FIG. 3 and FIG. 5. The RTP monitor call is established in step 406 of FIG. 4. The RTP monitor call 314 monitors the entire call 312 between the MTA 136a and the MTA 136b.

Following step 406, the method 400 shown in FIG. 4 continues to step 408 in which the call agent 108 creates a connection between the MTA 136a and the MTA 136b. The connection established in step 408 acts to create the voice call 312 shown in FIG. 3 and FIG. 5. The connection established in 408 includes signals 508, 510, 512, 514, and 516 shown in FIG. 5. A dial tone on signal that is input by the user dialing the handset in the CPE 101a is transmitted from the call agent to the MTA 136a as signal 508. Following the reception of the dial tone on signal, or at the CPE 101a, the user at the CPE 101a dials the desired phone number with which the CPE 101a wishes to communicate. Following the dialing of the digits, a digit signal 510, shown in FIG. 5, is transmitted from the MTA 136a to the call agent 108. The call agent using the components of the computer 190, after receiving the digit signal 510, establishes and transmits a connection CRCX signal 512 to act to create the RTP call 312 established between the MTA 136a and MTA 136b, as shown in FIGS. 3 and 5. All in the reception of the CRCX signal 512 at the MTA 136b, ring is created at the CPE 101b. This ringer is contained in the CPE to create the telephone ring in the associated subscriber telephone.

Following of the reception of the telephone ring 514, the CPE 101b will go offhook as indicated at 516 if either a user, an answering machine, or a facsimile machine responds to answer the telephone, or if any other known off hook condition occurs. Following the off hook signal 516, the RTP call 312 is established between the media terminal adapter (MTA) 136a of the CPE 101a and the MTA 136b of the CPE 101b. RTP call 312 occurs without the users of CPE 101a and CPE 101b having any knowledge of the concurrent RTP monitor call 314 shown in FIG. 3 and FIG. 5. As shown in FIG. 4, the RTP call is established as long as desired between the MTA 136a and MTA 136b. Following step 410, the method 400 continues to step 412 in which the RTP call and the RTP monitor call are terminated. The termination typically occurs by the ending of the RTP call 312 by either the CPE 101a or the CPE 101b user. Such RTP call 312 terminates also limits the production of the copy RTP packets from the RTP mirror 270 to the RTP server 152. Since no original RTP packets are being transmitted in call 312, no copy RTP packets will be transmitted in the monitor call 314.

The user at the call monitor device 154 can also terminate the monitor call 314 even though the RTP call 312 is continued. Under these circumstances, the RTP call 312 would continue, including the transmission of the original RTP packets between the MTA 136a and the MTA 136b, without any corresponding copy RTP packets being transmitted from the RTP mirror 270 to the RTP server 152 to form the RTP monitor call 314.

Figure 6:
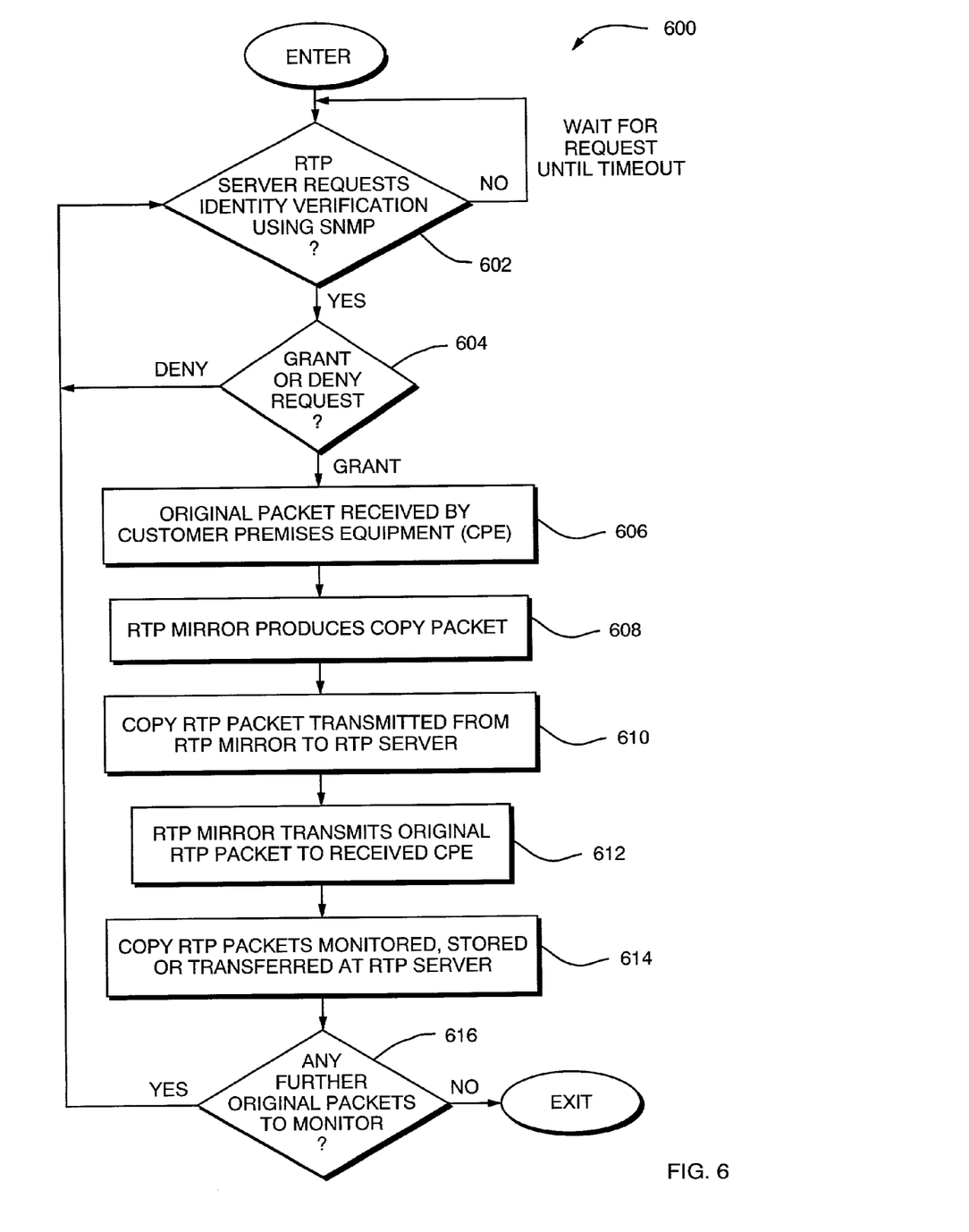
FIG. 6 shows one embodiment of a flow chart describing the procedure of making a copy RTP packet from an original packet.

The CPU 253, in one embodiment, performs the method 600 shown in FIG. 6. The method 600 begins with step 602 in which the RTP server 152 acting under the authority of such groups as the police to request identity verification. Such identity verification of the RTP server 152 is performed using SNMP v3 protocol. While simple network management protocol (SNMP) v3 is a protocol directed to the operation of a Management Information Base (MIB), the SNMP protocol also supports the level of security, as well. MIBs are commercially available database products that, in one embodiment, operate under the SNMP protocol that reside on such network servers 180 in communication with the IP network 106.

If the answer to decision step 602 is no, the method 600 continues to loop around until a request for RTP server 152 verification has been requested by the RTP server 152. If the answer to decision step 602 is yes, the method 600 continues to decision step 604 in which, if based on the received verification request, the verification is either granted or denied. If the answer to decision step 604 is to deny request, the method 600 continues looping to decision step 602. If the answer to decision step 604 is to grant request, the method 600 continues to step 606.

In step 606, the original RTP packet is received by CPE 101. As the original RTP packet travels through a portion of the CPE 101, it encounters the RTP mirror. In step 608, the RTP mirror operates by controllably producing a copy of the original RTP packet, when desired. The method 600 continues to step 610 in which the copy RTP packet is transmitted by the RTP mirror to the RTP server. The method 600 continues to step 612 in which the RTP mirror transmits the original RTP packets to travel to its original destination, be it the CPE 101 or remote 118.

The method 600 continues in step 614 in which the copy RTP packets are monitored, transferred, or stored at the RTP server 152. The packets that are being monitored at the RTP server 152 therefore include those RTP packets forming voice communications originating at the CPE 101 and being transmitted to the CPE 118. In addition, the copied RTP packets also include those RTP packets forming voice communications originating at the CPE 118 and being transmitted to the CPE 101. In this manner, both directions of voice conversation (duplex) using the VoIP to system 100 will be monitored at the RTP server 152. It is envisioned that, e.g., a personal computer with an audio outlet may be provided at the computer to allow listening to, or recording, conversations occurring at the CPE 101. Following step 614, the method 600 continues to decision step 616 in which it is determined whether there are any further original packets to be monitored. If the answer to 616 is no, then the method 600 is terminated. If the answer to decision step 616 is yes, then the method 600 loops back to decision step 602.

While the principles of the invention have been described above in connection with the specific apparatus and associated method, it is to be clearly understood that this description is made only by way of example and not as a limitation on the scope of the invention. For example, this disclosure was directed at monitoring voice communications between two CPEs and their associated subscriber telephones. However, it is envisioned that the above concepts can also be applied to monitoring voice communications between more than two CPEs and their associated subscriber telephones. While the above describes a VoIP system, the concepts may be applied to any applicable telephone system.

What is claimed:

1. An apparatus for monitoring voice over Internet (VoIP) signal communications originating from the customer premises equipment (CPE), the apparatus comprising:
  a real time protocol (RTP) mirror included in the CPE, the RTP mirror can be controllably altered between two mirror states, in both the first mirror state and the second mirror state the RTP mirror provides for transfer of original RTP packets to or from the CPE; in the first mirror state the RTP mirror limits transfer of a copy RTP packet from the RTP mirror, in the second mirror state the RTP mirror provides for transfer of the copy RTP packet from the RTP mirror.

2. The apparatus of claim 1, further comprising a network transferring original RTP packets between the CPE and a second CPE, wherein the network supports a packet switching protocol.

3. The apparatus of claim 1, further comprising:
  a network transferring copy RTP packets to or from the CPE; and
  a RTP server located on the network that receives those copy RTP packets generated by the RTP mirror.

4. The apparatus of claim 3, further comprising a Management Information Base (MIB) that verifies the identity of the RTP server.

5. The apparatus of claim 4, wherein the MIB uses the SNMP v3 protocol to verify the identity of the RTP server.

6. The apparatus of claim 4, wherein the RTP mirror can only be changed to the second mirror state if the MIB verifies the identity of the RTP server.

7. The apparatus of claim 1, further comprising a call agent, wherein the call agent establishes a RTP call that transfers the original RTP packets, and the call agent further establishes a RTP monitor call that transfers the copy RTP packets.

8. The apparatus of claim 1, wherein the RTP mirror is enabled when it is in the second mirror state.

9. The apparatus of claim 1 further comprising a network transferring original RTP packets between the CPE and at least a second CPE, wherein the network supports a packet switching protocol.

10. An apparatus that is configured to receive copy RTP packets that represent copies of original RTP packets transmitted between a plurality of consumer premises equipment (CPE), the apparatus comprising:
  a RTP server receiving copy RTP packets from a remote network location and that generates a RTP monitor call in response to the received copy RTP packets; and
  a real time protocol (RTP) mirror included in the customer premises equipment (CPE), the RTP mirror can be controllably altered between two mirror states, in both the first mirror state and the second mirror state the RTP mirror provides for transfer of original RTP packets to or from the CPE; in the first mirror state the RTP mirror limits transfer of copy RTP packets from the RTP mirror, in the second mirror state the RTP provides for transfer of the copy RTP packets.

11. A method of monitoring voice communications, comprising:
  identifying a first voice over Internet (VoIP) consumer premises equipment (CPE) to monitor voice communications;
  establishing an RTP call between the first VoIP CPE and a second CPE; and
  establishing an RTP monitor call between the first VoIP CPE and a RTP server,
  wherein the RTP call is established from an RTP mirror included in the first VoIP CPE.

12. The method of claim 11, wherein the RTP call is established using original RTP packets, and the monitor RTP call is made using copy RTP packets.

13. A method of monitoring voice communications, comprising:
  identifying a first voice over Internet (VoIP) consumer premises equipment (CPE) to monitor voice communications;
  establishing an RTP call between the first VoIP CPE and a second CPE; and
  establishing an RTP monitor call between the first VoIP CPE and a RTP server, and verifying the identity of the RTP server using a Management Information Base (MIB).

14. An apparatus for monitoring voice over Internet (VoIP) signal communications extending from a first customer premises equipment (CPE) to a second CPE, the apparatus comprising:
   a RTP server;
   a RTP mirror included in the first CPE, the RTP mirror can be controllably altered between two mirror states, in both the first mirror state and the second mirror state the RTP mirror provides for original RTP packet transfer between the first CPE to the second CPE, in the first mirror state the RTP mirror limits transfer of a copy RTP packet from the RTP mirror to the RTP server, in the second mirror state the RTP mirror provides for transfer of the copy RTP packet to the RTP server; and
   a call agent that first sets up a RTP monitor call that transfers the copy RTP packets from the RTP mirror to the RTP server, the call agent then establishes a regular call that transfers the original RTP packets from the first CPE to the second CPE.

15. The apparatus of claim 14, further comprising a Management Information Base (MIB) tat verifies the identity of the RTP server to place the RTP mirror in the second mirror state.

16. A method for monitoring telephone communications extending from a first customer premises equipment (CPE) to a second CPE, the method comprising:
   controllably altering a real time protocol (RTP) mirror between two mirror states, the RTP mirror providing for original RTP packet transfer from the first CPE to the second CPE in both the first mirror state and the second mirror state, limiting transfer of a copy RTP packet from the RTP mirror to a RTP server in the first mirror state;
   providing for transfer of the copy RTP packet from the RTP mirror to the RTP server in the second mirror state;
   providing for transfer of the original RTP packets from the first CPE to the second CPE; and
   establishing a RTP monitor call that transfers the copy RTP packets from the RTP mirror to the RTP server.

17. The method of claim 16, further comprising verifying the identity of the RTP server prior to any copy RTP packets are transmitted from the RTP mirror to the RTP server.

18. The method of claim 16, further comprising the instance of RTP mirror can be located on the CMTS which controls the first CPE.

* * * * *